(12) United States Patent
Kohlstruk et al.

(10) Patent No.: US 6,703,471 B2
(45) Date of Patent: Mar. 9, 2004

(54) PREPARATION OF LOW-ODOR-STORAGE-STABLE MONOMER-CONTAINING POLYISOCYANURATES BASED ON ISOPHORONE DIISOCYANTE

(75) Inventors: Stephan Kohlstruk, Duelmen (DE); Manfred Kreczinski, Herne (DE); Rainer Lomölder, Muenster (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/180,016

(22) Filed: Jun. 27, 2002

(65) Prior Publication Data

US 2003/0009054 A1 Jan. 9, 2003

(30) Foreign Application Priority Data

Jul. 2, 2001 (DE) .......................... 101 31 525

(51) Int. Cl.$^7$ .............................. C08G 18/20
(52) U.S. Cl. .......................... 528/54; 528/52; 528/45; 528/73; 252/182.2; 544/193; 544/222
(58) Field of Search .................. 544/222, 193; 528/45, 73, 52, 54; 252/182.2

(56) References Cited

U.S. PATENT DOCUMENTS

| | | | |
|---|---|---|---|
| 3,996,223 A | | 12/1976 | Gupta et al. |
| 4,040,992 A | * | 8/1977 | Bechara et al. |
| 4,186,255 A | | 1/1980 | Klein et al. |
| 4,324,879 A | | 4/1982 | Bock et al. |
| 4,454,317 A | * | 6/1984 | Disteldorf |
| 4,503,226 A | | 3/1985 | Tang et al. |
| 4,540,781 A | | 9/1985 | Barsa |
| 4,596,678 A | | 6/1986 | Merger et al. |
| 4,596,679 A | | 6/1986 | Hellbach et al. |
| 4,697,014 A | | 9/1987 | Robin |
| 5,087,739 A | | 2/1992 | Bohmholdt et al. |
| 5,221,743 A | | 6/1993 | Goldstein et al. |
| 5,258,482 A | | 11/1993 | Jacobs et al. |
| 6,093,817 A | | 7/2000 | Kohlstruk et al. |
| 6,452,003 B1 | | 9/2002 | Ewald et al. |
| 6,552,154 B1 | | 4/2003 | Kohlstruk et al. |

FOREIGN PATENT DOCUMENTS

| | | |
|---|---|---|
| CA | 2113890 | 8/1994 |
| DE | 26 31 733 | 2/1977 |
| EP | 0 003 765 | 9/1979 |
| EP | 017998 | 10/1980 |
| EP | 056159 | 7/1982 |
| EP | 126299 | 11/1984 |
| EP | 0126300 | 11/1984 |
| EP | 197864 | 10/1986 |
| EP | 0355443 | 2/1990 |
| EP | 524501 | 1/1993 |
| EP | 798299 | 10/1997 |
| EP | 1 170 283 | 1/2002 |
| WO | WO 99/36455 | 7/1999 |

OTHER PUBLICATIONS

Annalen der Chemie 562 (1949) 75 ff.

* cited by examiner

Primary Examiner—Rachel Gorr
(74) Attorney, Agent, or Firm—Oblon, Spivak, McClelland, Maier & Neustadt, P.C.

(57) ABSTRACT

Low-odor, storage-stable monomer-containing polyisocyanurate is prepared from isophorone diisocyanate by conducting a partial trimerization for 3 minutes to 3 hours in the presence of 0.05–2% by weight of a catalyst, based on the weight of the diisocyanate, the catalyst having the formula $$[R-NX_3]^{m\oplus} mY^\ominus$$

wherein $Y^\ominus$ is a carboxylic acid anion of 4–8 carbons, R is a β-hydroxyalkyl group of 2–6 carbons, X is an alkylene group of 2–3 carbons and m is a number from 1.0 to 2.0. The three radicals X form a ring with the quaternary nitrogen by way of a common nitrogen atom, which may be partly β-hydroxyalkylated, said ring optionally having an OH group positioned α, β or γ to the nitrogen. The reaction proceeds at a temperature of 0–160° C.

20 Claims, No Drawings

PREPARATION OF LOW-ODOR-STORAGE-STABLE MONOMER-CONTAINING POLYISOCYANURATES BASED ON ISOPHORONE DIISOCYANTE

BACKGROUND OF THE INVENTION

1. Field of the Invention

The present invention relates to a process for preparing a low-odor, and storage-stable, monomer-containing polyisocyanurate based on isophorone diisocyanate.

2. Discussion of the Background

As polyisocyanate adducts, polyisocyanurates are valuable components in the production of high-grade coatings having good mechanical properties and also good light stability and weather resistance. Polyisocyanurates based on isophorone diisocyanate (IPDI) are also used as raw materials for PU-based elastomer applications. It may be desirable for the IPDI-based polyisocyanurate, also referred to as IPDI trimer, to be used in a form which still includes monomer.

Polyisocyanurates are basically obtained by catalytic trimerization of appropriate isocyanates. Examples of appropriate isocyanates are aromatic, cycloaliphatic, and aliphatic diisocyanates and higher polyisocyanates. Examples of suitable catalysts include tertiary amines (U.S. Pat. No. 3,996,223), alkali metal salts of carboxylic acids (CA 2113890; EP 56159), quaternary ammonium salts (EP 798299; EP 524501; U.S. Pat. Nos. 4,186,255; 5,258,482; 4,503,226; 5,221,743), aminosilanes (EP 197864; U.S. Pat. No. 4,697,014), and quaternary hydroxyalkylammonium salts (EP 17998; U.S. Pat. No. 4,324,879). Depending on the catalyst it is also possible to use various cocatalysts, for example, OH-functionalized compounds or Mannich bases composed of secondary amines and aldehydes and/or ketones.

For trimerization, the polyisocyanates are reacted in the presence of the catalyst, where appropriate using solvents and/or auxiliaries, until the desired conversion has been achieved. In this context, one also speaks of partial trimerization, since the target conversion is generally well below 100%. The reaction is then terminated by deactivating the catalyst. This is done by adding a catalyst inhibitor such as, for example, p-toluenesulfonic acid, hydrogen chloride or dibutyl phosphate, and results unavoidably in a possibly unwanted contamination of the polyisocyanate containing isocyanurate groups that are formed. Of particular advantage in respect of the trimerization of isocyanates on the industrial scale is the use of quaternary hydroxyalkylammonium carboxylates as oligomerization catalysts. This type of catalyst is thermally labile and is amenable to targeted thermal deactivation, so that it is unnecessary to stop the trimerization by adding potentially quality-reducing inhibitors when the desired conversion has been reached.

Monomer-containing IPDI trimer, which is suitable, for example, for the abovementioned PU injection applications, has an NCO content of 28–32% by weight. The polyisocyanurate is prepared by partial trimerization of IPDI in the presence of one or more appropriate catalysts. Afterward, the catalyst must either be removed fully from the reaction solution—this can be done by short-path or thin-film distillation—or deactivated, because the trimer lacks storage stability in the presence of active catalyst residues. Where the NCO content of the IPDI polyisocyanurate obtained is below the desired level, it can be adjusted as desired without problems by diluting the solution with monomeric IPDI.

Alkali metal salts of carboxylic acids are not very suitable as catalysts for preparing monomer-containing IPDI trimer, because they are difficult, if not impossible, to remove from the reaction product. With regard to the amine catalysts available, it has been found that the resulting IPDI trimer solutions are fundamentally hampered by a clearly perceptible odor, which is sufficiently pronounced to remain detectable in the end application and to manifest itself unpleasantly. In order to eliminate the odor nuisance, it is technical practice to free the reaction solution, following partial trimerization and catalyst deactivation, from excess IPDI, from odoriferous components, and, where appropriate, from unwanted catalyst inhibitors. This is generally done by means of short-path or thin-film distillation. Subsequently, the monomer-freed solid resin is converted into the desired, low-odor and monomer-containing IPDI polyisocyanurate by adding fresh IPDI.

The sequence of partial trimerization/deactivation, demonomerization/purification, and, finally, dissolution of the solid resin in the monomer is very cumbersome. The step of separating off the monomer in the existing process consumes a lot of time, adds a lot of costs, and, moreover, represents a capacity-limiting bottleneck.

SUMMARY OF THE INVENTION

It is therefore an object of the present invention to provide a more economical process for preparing a low-odor and storage-stable monomer-containing polyisocyanurate based on isophorone diisocyanate, in which demonomerization is avoided. It has surprisingly been found that this step can in fact be omitted and, moreover, that the use of possibly quality-reducing inhibitors can be avoided if the trimerization of IPDI is conducted in the presence of specific catalysts.

Accordingly, the present invention provides for a process for preparing a low-odor, storage-stable monomer-containing polyisocyanurate, comprising:

partially trimerizing isophorone diisocyanate at a temperature of 0–160° C. for 3 minutes to 3 hours in the presence of 0.05–2% by weight of a catalyst, based on the weight of the isophorone diisocyanate;

wherein said catalyst is represented by the following formula

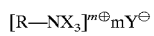

wherein $Y^\ominus$ is a carboxylic acid anion having 4–8 carbons;

R is a β-hydroxyalkyl group having 2–6 carbons;

X is an alkylene group having 2–3 carbons; and m is a number from 1.0 to 2.0;

wherein the three radicals X form a ring with the quaternary nitrogen by way of a common nitrogen atom; and wherein said process proceeds at a temperature of from 0 to 160° C.

DETAILED DESCRIPTION OF THE INVENTION

The present invention provides a process for preparing a low-odor, storage-stable monomer-containing polyisocyanurate from isophorone diisocyanate. The process comprises conducting a partial trimerization of isophorone diisocyanate over a period of 3 minutes to 3 hours in the presence of 0.05–2% by weight of a catalyst, based on the weight of the diisocyanate, the catalyst having the general formula

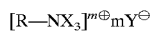

wherein $Y^\ominus$ is a carboxylic acid anion of 4–8 carbons,

R is a β-hydroxyalkyl group of 2–6 carbons,

X is an alkylene group of 2–3 carbons, and m is a number from 1.0 to 2.0. The three radicals X form a ring with the quaternary nitrogen by way of a common nitrogen atom, which may be partly β-hydroxyalkylated, said ring possibly having an OH group positioned α, β or γ to the nitrogen. The process proceeds at a temperature of 0–160° C., preferably 40–120° C., and most preferably 55–95° C. In this it is possible to dispense with separating off the monomer and chemically deactivating the trimerization catalyst. The reaction temperature includes all values and subvalues therebetween, especially including 10, 20, 30, 40, 50, 60, 70, 80, 90, 100, 110, 120, 130, 140 and 150° C. The reaction time of the partial trimerization includes all values and subvalues therebetween, especially including 5, 10, 20, 30, 40, 50, 60, 70, 80, 90, 100, 110, 120, 130, 140, 150, 160 and 170 min. The amount of catalyst includes all values and subvalues therebetween, especially including 0.1, 0.2, 0.3, 0.4, 0.5, 0.6, 0.7, 1, 1.1, 1.2, 1.3, 1.4, 1.5, 1.6, 1.7, 1.8 and 1.9%.

In principle, isocyanates appropriate for trimerization can be prepared by different kinds of processes (Annalen der Chemie 562 (1949) 75 ff.). Particularly well established in the industry is their preparation by phosgenating organic polyamines to the corresponding polycarbamoyl chlorides and cleaving these chlorides thermally into organic polyisocyanates and hydrogen chloride. Alternatively, organic polyisocyanates can also be prepared without using phosgene, i.e., by phosgene-free processes. According to EP-A-126 299 (U.S. Pat. No. 4,596,678), EP-A-126 300 (U.S. Pat. No. 4,596,679), and EP-A-355 443 (U.S. Pat. No. 5,087,739), for example, (cyclo)aliphatic diisocyanates, such as 1-isocyanato-3-isocyanatomethyl-3,5,5-trimethylcyclohexane (isophorone diisocyanate, IPDI), can be made available by reacting the parent (cyclo)aliphatic diamines with urea and alcohols to give (cyclo)aliphatic biscarbamic esters, and thermally cleaving these esters into the corresponding diisocyanates and alcohols.

For the process of the present invention for preparing low-odor, storage-stable monomer-containing polyisocyanurates based on isophorone diisocyanate it is unimportant by which synthetic pathway the IPDI used has been prepared. It may be noted, however, that one of the factors affecting the amount of catalyst required for achieving a desired NCO content is the quality of the raw material. The NCO is 22–34% by weight, especially including 23, 24, 25, 26, 27, 28, 29, 30, 31, 32 and 33% by weight. From experience, increasing levels of hydrolyzable chlorine compounds in the IPDI necessitate an increase in the amount of catalyst. It appears that the hydrolyzable chlorine tends to have an inhibiting effect on the catalyst.

The preparation of the low-odor, storage-stable monomer-containing polyisocyanurates based on isophorone diisocyanate by partial trimerization, in accordance with the invention, may take place continuously (tube reactor or tank cascade) or else may be conducted batchwise. The catalyst is used at a low concentration of between 0.05 and 2% by weight. The precise amount can be determined experimentally with ease and is dependent on the catalyst, on the target conversion, on the quality of the IPDI used, and on the procedure.

The partial trimerization may be conducted within a period of from 3 minutes to 3 hours. The product contains monomeric IPDI, trimeric IPDI isocyanurate, and higher oligomers with an isocyanurate structure. As a secondary component, minor amounts of compounds with a uretdione structure may also be found. Compounds of this kind are described in the literature.

In accordance with the present invention the catalyst is used in an amount of 0.05–2% by weight, based on the weight of the isophorone diisocyanate used. The catalyst is easy to obtain by reacting the three building blocks—tricyclic diamine, carboxylic acid, and oxirane. Where appropriate, it may be prepared in the presence of a solvent. It is common to use alcohols of low molecular mass such as methanol or ethylene glycol. One example of a suitable tricyclic diamine is diazabicyclo[2.2.2]octane. Examples of suitable carboxylic acids are acetic acid, hexanoic acid, and 2-ethylhexanoic acid. Possible options for the oxirane component include, for example, propylene oxide, butylene oxide or 1,2-epoxyhexane. The molar ratios of the three building blocks for preparing the catalysts used in accordance with the invention are variable. Depending on the proportions of the building blocks, catalysts having at least one quaternary nitrogen atom in the molecule are obtained. As the examples show, catalysts possessing in some cases more than two quaternary nitrogen atoms are also used.

The process of the present invention is conducted at temperatures between 0° C. and 160° C., preferably between 40° C. and 120° C., and, with particular preference, between 55 and 95° C.

In accordance with the present invention, the partial trimerization of the isophorone diisocyanate is conducted either batchwise or continuously. The batch process is preferred.

In the case of the batch process, operation takes place in a stirred reactor. The isophorone diisocyanate is introduced as initial charge. The catalyst is metered in after the IPDI has reached the temperature required for reaction: 0–140° C., preferably 55–90° C., particularly preferably 65–75° C. The temperature includes all values and subvalues therebetween, especially including 10, 20, 30, 40, 50, 60, 70, 80, 90, 100, 110, 120 and 130° C. The trimerization is exothermic. The catalyst is first of all metered in in an amount such that a marked rise in the temperature of the reaction mixture by 5–15° C. occurs. The rise in temperature includes all values and subvalues therebetween, especially including 6, 7, 8, 9, 10, 11, 12, 13 and 14° C. Since the catalyst is deactivated in the course of the reaction, the temperature of the reaction mixture drops again during the reaction, and a further addition of catalyst may be made. This procedure is repeated until the desired conversion has been reached. The sequence of catalyst deactivation and reinitiation of the trimerization by addition of further portions of catalyst means that it is readily possible at any time to monitor the process in respect to both, the conversion and the temperature profile of the reaction.

The catalyst may be used in neat form. For more precise metering and optimum mixing of the catalyst, however, it is advantageous to dissolve the catalyst in an appropriate solvent. Appropriate solvents include in principle all those possessing good solvency for the catalyst: examples include water, alcohols of low molecular mass such as methanol or ethylene glycol, or organic acids of low molecular mass such as acetic or hexanoic acid, for example.

The continuous trimerization may be conducted in a tank cascade. A combination of tank cascade and tube reactor is also possible.

In order to restrict the required amount of catalyst relative to the desired conversion, the temperature profile of the process of the invention should as far as possible be configured so that the reaction solution does not exceed a temperature of 95° C., preferably 85° C., more preferably 75° C. and most preferably 65° C.

The low-odor, storage-stable monomer-containing polyisocyanurates based on isophorone diisocyanate that are prepared in accordance with the present invention are useful intermediates for polyurethane coatings, polyurethane and polyurea moldings, as produced, for example, by the RIM (reaction injection molding) process, for polyurethane injection applications, or else for polyurethane-based automobile window sealing. They may be used in a form in which they have been blocked with blocking agents. Examples of suitable blocking agents in this case include lactams, such as ε-caprolactam, oximes, such as methyl ethyl ketoxime or butanone oxime; triazoles, such as 1H-1,2,4-triazole; readily enolyzable compounds, such as acetoacetates or acetylacetone; or else malonic acid derivatives, such as malonic diesters. The blocking agents can be used alone or in combination.

Having generally described this invention, a further understanding can be obtained by reference to certain specific examples which are provided herein for purposes of illustration only, and are not intended to be limiting unless otherwise specified.

EXAMPLES

Catalyst Preparation
Catalyst 1
70% by weight of a mixture of butylene oxide, 2-ethylhexanoic acid and diazabicyclo[2.2.2]octane (molar ratio 1:1:1) were stirred in the presence of 30% by weight of ethylene glycol at room temperature for 3 days.
Catalyst 2
70% by weight of a mixture of propylene oxide, 2-ethylhexanoic acid and diazabicyclo[2.2.2]octane (molar ratio 1:1:1) were stirred in the presence of 30% by weight of ethylene glycol at room temperature for 3 days.
Catalyst 3
60% by weight of a mixture of propylene oxide, 2-ethylhexanoic acid and diazabicyclo[2.2.2]octane (molar ratio 1.25:1.25:1.12) were stirred in the presence of 40% by weight of ethylene glycol at room temperature for 3 days.
Catalyst 4
80% by weight of a mixture of propylene oxide, 2-ethylhexanoic acid and diazabicyclo[2.2.2]octane (molar ratio 1.4:1.4:1) were stirred in the presence of 20% by weight of methanol at room temperature for 3 days.
Trimerization Experiments:
The reaction of Examples 1–4 according to the present invention and Comparative Examples 1–6 took place under an $N_2$ atmosphere.

Examples 1–4 According to the Present Invention

B.1. Trimerization of IPDI Using Catalyst 1
800 g of IPDI were admixed at 70° C. with 2.0 g (0.25% by weight) of catalyst 1 in portions. The temperature of the mechanically stirred reaction mixture rose to a maximum of 87° C. and then fell again gradually. Further catalyst was then added in small portions, so that the temperature of the reaction solution varied within the range of 81–90° C. Following the addition of a total of 3.9 g (0.49% by weight) of catalyst 1, the reaction mixture reached an NCO content of less than 29% by weight. It was cooled to room temperature. The NCO content of the low-odor reaction product was 28.2% and remained stable even after storage for 7 days at 20–30° C.

B.2. Trimerization of IPDI Using Catalyst 2
800 g of IPDI were admixed at 70° C. with 2.0 g (0.25% by weight) of catalyst 2 in portions. The temperature of the mechanically stirred reaction mixture rose to a maximum of 89° C. and then fell again gradually. Further catalyst was then added in small portions, so that the temperature of the reaction solution varied within the range of 78–90° C. Following the addition of a total of 3.7 g (0.46% by weight) of catalyst 2, the reaction mixture reached an NCO content of less than 29% by weight. It was cooled to room temperature. The NCO content of the low-odor reaction product was 28.4% and remained stable even after storage for 7 days at 20–30° C.

B.3. Trimerization of IPDI Using Catalyst 3
50 kg of IPDI were admixed at 70° C. with 102 g (0.20% by weight) of catalyst 3 in portions. The temperature of the mechanically stirred reaction mixture rose to a maximum of 85° C. and then fell again gradually. Further catalyst was then added in small portions, so that the temperature of the reaction solution varied within the range of 83–92° C. Following the addition of a total of 223 g (0.45% by weight) of catalyst 3, the reaction mixture reached an NCO content of less than 29% by weight. It was cooled to room temperature. The NCO content of the low-odor reaction product was 28.1% and remained stable even after storage for 7 days at 20–30° C.

B.4. Trimerization of IPDI Using Catalyst 4
50 kg of IPDI were admixed at 70° C. with 110 g (0.22% by weight) of catalyst 4 in portions. The temperature of the mechanically stirred reaction mixture rose to a maximum of 86° C. and then fell again gradually. Further catalyst was then added in small portions, so that the temperature of the reaction solution varied within the range of 82–94° C. Following the addition of a total of 220 g (0.44% by weight) of catalyst 4, the reaction mixture reached an NCO content of less than 29% by weight. It was cooled to room temperature. The NCO content of the low-odor reaction product was 28.4% and remained stable even after storage for 7 days at 20–30° C.

Comparative Examples

B.5. Trimerization of IPDI Using Dabco TMR$^R$
1500 g of IPDI were admixed at 80° C. with 3.75 g (0.25% by weight) of Dabco TMR$^R$ (N-(2-hydroxypropyl)-N,N,N-trimethylammonium 2-ethylhexanoate, approximately 75% in diethylene glycol). Due to the strongly exothermic course of the reaction, the temperature of the mechanically stirred reaction mixture rose over the course of about 3 minutes to reach a peak of 136° C. The reaction mixture was cooled to room temperature. The NCO content of the reaction product, which had a strong amine odor, was 28.9% and remained stable even after storage for 7 days at 20–30° C.

In order to eliminate the odor problem, unreacted IPDI was separated off from the polyisocyanurate by short-path evaporation. After the monomer-freed resin had been diluted with fresh IPDI to an NCO content of 29.6%, a low-odor monomer-containing IPDI trimer was obtained.

B.6. Trimerization of IPDI Using Dabco TMR$^R$-2
1500 g of IPDI were admixed at 80° C. with 3.75 g (0.25% by weight) of Dabco TMR$^R$-2 (N-(2-hydroxypropyl)-N,N,N-trimethylammonium formate, approximately 75% in diethylene glycol). Due to the strongly exothermic course of the reaction, the temperature of the mechanically stirred reaction mixture rose over the course of about 3 minutes to reach a peak of 139° C. The reaction mixture was cooled to room temperature. The NCO content of the reaction product, which had a strong amine odor, was 28.2% and remained stable even after storage for 7 days at 20–30° C.

In order to eliminate the odor problem, unreacted IPDI was separated off from the polyisocyanurate by short-path evaporation. After the monomer-freed resin had been diluted with fresh IPDI to an NCO content of 29.6%, a low-odor monomer-containing IPDI trimer was obtained.

B.7. Trimerization of IPDI using N-(2-hydroxypropyl)-N,N,N-trimethylammonium hydroxide 1500 g of IPDI were admixed at 80° C. with 3.75 g (0.25% by weight) of N-(2-hydroxypropyl)-N,N,N-trimethylammonium hydroxide (approximately 75% in diethylene glycol). Owing to the strongly exothermic course of the reaction, the temperature of the mechanically stirred reaction mixture rose over the course of about 3 minutes to reach a peak of 143° C. The reaction mixture was cooled to room temperature. The NCO content of the reaction product, which had a strong amine odor, was 27.6% and remained stable even after storage for 7 days at 20–30° C.

In order to eliminate the odor problem, unreacted IPDI was separated off from the polyisocyanurate by short-path evaporation. After the monomer-freed resin had been diluted with fresh IPDI to an NCO content of 29.6%, a low-odor monomer-containing IPDI trimer was obtained.

B.8. Trimerization of IPDI using hexamethyldisilazane (HMDS)

1600 g of IPDI were admixed at 100° C. with 1.6 g (1% by weight, 0.1 mol) of HMDS. When, after 30 minutes, no reaction was observed, the temperature of the mechanically stirred reaction mixture was raised to 120° C. Even under these conditions, no significant conversion was achievable. The batch was cooled to 50° C. and the catalyst was deactivated by adding 0.9 g (0.05 mol) of water. The reaction solution had an NCO content of 37.2% and gave off an aminelike odor. Due to the low conversion, no attempt was made to eliminate the odor problem by short-path evaporation and subsequent dilution of the monomer-freed resin with fresh IPDI.

B.9. Trimerization of IPDI Using Dabco TMR$^R$ 1500 g of IPDI were admixed at 70° C. with 2.2 g (0.15% by weight) of Dabco TMR$^R$ (N-(2-hydroxypropyl)-N,N,N-trimethylammonium 2-ethylhexanoate, approximately 75% in diethylene glycol). The temperature of the mechanically stirred reaction mixture rose to a peak of 75° C. The temperature of the reaction mixture was held at a level of 70–75° C. without further addition of catalyst. When the NCO content of the reaction mixture had fallen below 29% by weight, it was cooled to room temperature. The NCO content of the reaction product, which had a strong amine odor, was 28.3%. The reaction product was not stable on storage. During storage for 7 days at 20–30° C., the NCO content fell as a function of time.

In order to eliminate the odor problem, unreacted IPDI was separated off from the polyisocyanurate by short-path evaporation. After the monomer-freed resin had been diluted with fresh IPDI to an NCO content of 29.6%, a low-odor monomer-containing IPDI trimer was obtained.

B.10. Trimerization of IPDI Using Dabco TMR$^R$-2

1500 g of IPDI were admixed at 70° C. with 2.4 g (0.16% by weight) of Dabco TMR$^R$-2 (N-(2-hydroxypropyl)-N,N,N-trimethylammonium formate, approximately 75% in diethylene glycol). The temperature of the mechanically stirred reaction mixture rose to a peak of 76° C. The temperature of the reaction mixture was held at a level of 70–75° C. without further addition of catalyst. When the NCO content of the reaction mixture had fallen below 29% by weight, it was cooled to room temperature. The NCO content of the reaction product, which had a strong amine odor, was 28.5%. The reaction product was not stable on storage. During storage for 7 days at 20–30° C., the NCO content fell as a function of time.

In order to eliminate the odor problem, unreacted IPDI was separated off from the polyisocyanurate by short-path evaporation. After the monomer-freed resin had been diluted with fresh IPDI to an NCO content of 29.6%, a low-odor monomer-containing IPDI trimer was obtained.

TABLE 1

Trimerizations of IPDI (Examples B.1.–B.4. according to the present invention and Comparative Examples B.5.–B.10.)

| Experiment | Category | Catalyst | Amount of catalyst [wt. %] | NCO content [wt. %] | Remarks |
|---|---|---|---|---|---|
| B.1. | Present invention | Catalyst 1 | 0.49 | 28.2 | storage stable, low odor |
| B.2. | Present invention | Catalyst 2 | 0.46 | 28.4 | storage stable, low odor |
| B.3. | Present invention | Catalyst 3 | 0.45 | 28.1 | storage stable, low odor |
| B.4. | Present invention | Catalyst 4 | 0.44 | 28.4 | storage stable, low odor |
| B.5. | Comparative | Dabco TMR$^R$ | 0.25 | 28.9 | storage stable, marked odor |
| B.6. | Comparative | Dabco TMR$^R$-2 | 0.25 | 28.2 | storage stable, marked odor |
| B.7. | Comparative | N-(2-hydroxy-propyl)-N,N,N-tri-methyl-ammonium hydroxide | 0.25 | 27.6 | storage stable, marked odor |
| B.8. | Comparative | Hexamethyl disilazane | 1.0 | 37.2 | storage stable, marked odor |
| B.9. | Comparative | Dabco TMR$^R$ | 0.15 | 28.3 | not storage-stable, marked odor given off |
| B.10 | Comparative | Dabco TMR$^R$-2 | 0.16 | 28.5 | not storage stable, marked odor given off |

German patent application 101 31 5251.2, filed Jul. 7, 2001, is incorporated herein by reference.

Numerous modifications and variations on the present invention are possible in light of the above teachings. It is therefore to be understood that within the scope of the appended claims, the invention may be practiced otherwise than as specifically described herein.

What is claimed is:

1. A process for preparing a monomer-containing polyisocyanurate, comprising:

partially trimerizing isophorone diisocyanate at a temperature of 0–160° C. for 3 minutes to 3 hours in the presence of 0.05–2% by weight of a catalyst, based on the weight of the isophorone diisocyanate;

wherein said catalyst is represented by the following formula

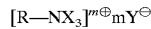

$$[R-NX_3]^{m\oplus} mY^{\ominus}$$

wherein $Y^{\ominus}$ is a carboxylic acid anion having 4–8 carbons;

R is a β-hydroxyalkyl group having 2–6 carbons;

X is an alkylene group having 2–3 carbons; and m is a number from 1.0 to 2.0;

wherein the three radicals X form a ring with the quaternary nitrogen by way of a common nitrogen atom; and wherein said process proceeds at a temperature of from 0 to 160° C.

2. The process according to claim 1, wherein said common nitrogen atom is optionally partly β-hydroxyalkylated.

3. The process according to claim 1, wherein said ring optionally has an OH group positioned α, β or γ to the nitrogen.

4. The process according to claim 1, wherein said isophorone diisocyanate has been prepared by a phosgene process or by a phosgene-free process.

5. The process according to claim 1, wherein said monomer-containing polyisocyanurate has an NCO content of 22–34% by weight.

6. The process according to claim 1, wherein the reaction takes place at a temperature of from 40 to 120° C.

7. The process according to claim 1, wherein the reaction takes place at a temperature of from 55 to 95° C.

8. The process according to claim 1, wherein no separation of monomer is performed.

9. The process according to claim 1, wherein no chemical deactivation of said catalyst is performed.

10. The process according to claim 1, wherein the catalyst is obtained by reacting a tricyclic diamine, a carboxylic acid, and an oxirane.

11. The process according to claim 1, wherein said process is conducted batchwise.

12. The process according to claim 11, wherein the isophorone diisocyanate is introduced as an initial charge; and wherein said catalyst is metered in after the isophorone diisocyanate has reached a temperature of 0–140° C.

13. The process according to claim 1, which is conducted in a tank cascade.

14. A monomer-containing polyisocyanurate obtained by the process according to claim 1.

15. The polyisocyanurate according to claim 14, which is blocked with a blocking agent.

16. The polyisocyanurate according to claim 15, wherein said blocking agent is selected from the group consisting of lactams, oximes, triazoles, acetoacetate, acetylacetone, malonic acid derivatives and mixtures thereof.

17. The process according to claim 1 which is conducted continuously.

18. The process according to claim 1 which is conducted continuously in a tube reactor.

19. The process according to claim 1 which is conducted continuously in a tank cascade.

20. The process according to claim 1 which is conducted continuously in a tank cascade and a tube reactor.

* * * * *

UNITED STATES PATENT AND TRADEMARK OFFICE
CERTIFICATE OF CORRECTION

PATENT NO. : 6,703,471 B2
DATED : March 9, 2004
INVENTOR(S) : Kohlstruk et al.

It is certified that error appears in the above-identified patent and that said Letters Patent is hereby corrected as shown below:

<u>Title page, Item [54] and Column 1, Lines 1-2,</u>
Title, should read:
-- [54] PREPARATION OF LOW-ODOR-STORAGE-STABLE MONOMER-CONTAINING POLYISOCYANURATES BASED ON ISOPHORONE DIISOCYANATE --

Signed and Sealed this

First Day of June, 2004

JON W. DUDAS
*Acting Director of the United States Patent and Trademark Office*